(12) United States Patent
Suson et al.

(10) Patent No.: US 6,206,906 B1
(45) Date of Patent: *Mar. 27, 2001

(54) METHODS AND DEVICES FOR PERFORMING A TEMPORARY TARSORRHAPHY

(76) Inventors: John Suson, 4445 Danbury Dr., Brookfield, WI (US) 53045; Williford Smith, 4437 N. 55th St., Milwaukee, WI (US) 53218

( * ) Notice: Subject to any disclaimer, the term of this patent is extended or adjusted under 35 U.S.C. 154(b) by 0 days.

This patent is subject to a terminal disclaimer.

(21) Appl. No.: 09/184,626

(22) Filed: Nov. 2, 1998

(51) Int. Cl.[7] .................................................. A61B 17/04
(52) U.S. Cl. ............................................. 606/215; 128/898
(58) Field of Search .................................. 606/215, 216; 128/898, 858

(56) References Cited

U.S. PATENT DOCUMENTS

| | | |
|---|---|---|
| 3,103,218 | 9/1963 | Ajemian . |
| 4,134,401 | 1/1979 | Galician . |
| 4,696,301 | 9/1987 | Barabe . |
| 5,144,944 | 9/1992 | Rice ........................................ 602/74 |
| 5,214,093 | 5/1993 | Nell et al. . |
| 5,263,973 | 11/1993 | Cook ...................................... 606/216 |
| 5,290,292 | 3/1994 | Householder . |
| 5,542,437 | 8/1996 | Balckmore et al. . |
| 5,823,938 | * 10/1998 | Hernandez .............................. 600/15 |
| 6,034,292 | * 3/2000 | Mazaheri ............................... 602/41 |
| 6,034,293 | * 3/2000 | Stamler ................................. 602/41 |

OTHER PUBLICATIONS

Rapoza, Peter A., M.D. et al., "Temporary Sutured Tube-Tarsorrhaphy Reversible Eyelid Closure Technique", *Ophthalmic Surgery*, vol. 24, No. 5, pp. 328–330 (1993).

Fox, Sidney A., "Ophthalmic Plastic Surgery", Fourth Ed., Chapter 4, "Basic Techniques", pp. 73–87, 1970.

* cited by examiner

*Primary Examiner*—Gary Jackson
(74) *Attorney, Agent, or Firm*—Foley & Lardner (57) ABSTRACT

Devices and methods for performing a temporary tarsorrhaphy are provided. One device comprises two shafts mounted in parallel on the upper and lower eyelids of an eye. The shafts are then fastened together in a reversible manner to complete the temporary tarsorrhaphy. Each device further comprises a tube which is partially implanted in a linear fashion under the eyelid such that the tube is at a subcutaneous center portion and each end of the tube projects from the eyelid. The end portions of the tube that lie outside of the eyelid are each attached to the terminal portion of a shaft having first and second ends. The procedure is repeated on the lower eyelid. The shafts are then joined together with one or removable fasteners to complete the temporary tarsorrhaphy.

24 Claims, 7 Drawing Sheets

METHODS AND DEVICES FOR PERFORMING A TEMPORARY TARSORRHAPHY

TECHNICAL FIELD

The present invention relates generally to medical technology and to methods and devices for performing a temporary tarsorrhaphy.

BACKGROUND OF THE INVENTION

Tarsorrhaphy is a common ophthalmic procedure performed on damaged eyes involving surgical fusion of the upper and lower eyelid margins. The procedure has the effect of partially or fully narrowing the palpebral fissure, thereby reducing exposure of the damaged eye to the external environment, allowing the damaged eye to heal. This procedure is performed most commonly to protect an injured cornea. Examples of conditions which often call for a tarsorrhaphy include keratitis associated with severe dry eyes, non-healing corneal abrasions or ulcers due to any cause, and corneas which are in poor condition immediately following surgical procedures such as corneal transplant, vitrectomy, or glaucoma surgery with the use of antimetabolites, which in themselves are often injurious to the cornea.

The tarsorrhaphy may be one of two varieties. A permanent tarsorrhaphy may be formed wherein the eyelid margins are sealed indefinitely. More common is a procedure known as a temporary tarsorrhaphy wherein the eyelids are fastened together for a time period ranging from six weeks to several months.

Although several techniques exist for performing a temporary tarsorrhaphy, this fundamental procedure implies a surgery that is usually carried out by sewing the top and bottom eyelids together, using a fine suture. The simplest method of creating a tarsorrhaphy is to mark off the opposing areas of the upper and lower eyelids to be fused by means of scratch marks. The eyelids are then sutured together at the marks.

Several problems have been associated with temporary tarsorrhaphies. The sutures used to create the tarsorrhaphy may loosen or pull out before their function is fully accomplished. This may occur in lids whose vitality has been lowered by severe trauma or frequent surgical procedure. This also occurs in lids narrowed congenitally or by loss of tissue due to trauma. Various other techniques have been used in performing a temporary tarsorrhaphy to try to prevent the integrity of the sutures used in performing a tarsorrhaphy from being negatively impacted.

A complex tarsorrhaphy technique has been designed in which a tongue and groove are created in the lower and upper eyelids, respectively, and the tongue is then drawn up to fill the groove in the upper lid and sewn into place. However, in addition to the usual surgical problems associated with sewn-in-place tarsorrhaphies, this method requires more surgery, additional tissue disruption, and may require a longer healing time.

Other techniques also exist for performing a temporary tarsorrhaphy. Small rectangular pieces of material, known as "pegs", may be placed opposite each other on the upper and lower eyelids. The pegs are sewn to the eyelids and then to each other to accomplish the temporary tarsorrhaphy. Although this procedure is of some help in preventing loosening or tearing of the sutures, none of the temporary tarsorrhaphy methods to date have addressed the additional problem of being able to allow the eyelids to be separated in order to visualize the cornea or other parts of the eye without removing the temporary tarsorrhaphy itself.

Although it is possible to sew only a portion of the eyelids together in performing a temporary tarsorrhaphy, this allows only partial protection of the eye and allows only a portion of the eye to be inspected by the ophthalmic practitioner without removing the tarsorrhaphy. Since the purpose of the temporary tarsorrhaphy is to protect the eye and/or to promote healing, it would be advantageous to be able to easily open and reclose the eyelids at will to assess the status of the eye.

Temporary tarsorrhaphies are intended to last for a period of time ranging from six weeks to several months. However, it has been found that by using any of the known methods for a temporary tarsorrhaphy, the tarsorrhaphy can be expected to last a maximum of six weeks. Due to the very thin sutures used to tie the lids together, the sutures have a tendency to pull through or "cheesewire" through the thin tissue of the eyelids. It would be of great advantage if a temporary tarsorrhaphy could be performed which would prevent "cheesewiring", as well as allowing the entire eye to be viewed and allow the eyelids to be easily opened and reclosed without having to re-perform the tarsorrhaphy.

SUMMARY OF THE INVENTION

One object of the present invention is a method for performing a temporary tarsorrhaphy wherein a first tube is inserted in a linear fashion through a portion of the upper eyelid of an eye so that a portion of the first tube lies beneath the skin of the eyelid and each end of the first tube protrudes from the upper eyelid. A second tube having first and second ends is inserted through a portion of the lower eyelid of the eye in a linear fashion so that each end of the second tube also protrudes from the lower eyelid. The protruding ends of the first and second tubes preferably lie approximately parallel to the eyelid margin. The first ends of the first and second tubes are drawn and secured together in a reversible manner. The second ends of the first and second tubes are also drawn and secured together in a reversible manner to complete a temporary tarsorrhaphy.

Another object of the present invention is a device comprising a tarsorrhaphy clip further comprising a tube having first and second ends and a connecting means having first and second ends. A clip may be attached to each eyelid of an eye, and the clips are secured together in a reversible manner with one or more fasteners. To attach the first clip to the upper eyelid, a first tube is inserted in a linear fashion through a portion of the upper eyelid of an eye so that a portion of the tube lies beneath the skin of the eyelid, and each end of the tube protrudes from the upper eyelid. Preferably, the end portions of the tube that lie outside the skin of the eyelid are parallel to the palpebral fissure. A first connecting means is then placed between the two protruding ends of the first tube, and a portion of the first tube located proximate the first end of the tube is attached to the first end of the first connecting means. The first tube is then drawn taut, and the second end of the first connecting means tube is attached to a portion of the tube proximate the second end of the first tube, such that the connecting means secures portions of the first tube which protrude from the eyelid, completing placement of the first clip. Once secured in place, the first clip lies approximately parallel to the palpebral fissure.

A similar procedure is used to attached the second clip to the lower eyelid of the eye. A second tube having first and second ends is inserted through a portion of the lower eyelid of the eye in a linear fashion so that each end of the second tube also protrudes from the lower eyelid. A portion of the second tube proximate to the first end of the tube is attached to the first end of a second connecting means. The second tube is then drawn taut, and a portion of the second tube proximate the second end of the tube is firmly secured to the second end of the second connecting means. The second clip is positioned on the eyelid approximately parallel to the palpebral fissure.

In a preferred embodiment, the connecting means each comprise a metal rod, each have a cylindrical sleeve covering the mid portion of each rod to protect the eyelid from abrasion. Additionally, in the preferred embodiment, each end of each connecting means comprises a small jawed clamp which can be locked down to hold a portion of a tube. In the preferred embodiment, after the ends of each tube have been secured by the connecting means, a small cap is placed over the ends of each jawed clamp to lock the clamp closed, if the jawed clamps are not self-locking.

After the first and second clips are attached to the eyelids, the eye is then closed so that the first connecting means on the upper eyelid and the second connecting means on the lower eyelid lie approximately parallel in close proximity to each other across the palpebral fissure. The first ends of each connecting means situated distal to the nose are bound together with one or more removable fasteners, preferably elastic bands. The second ends of each connecting means located proximate to the nose are then secured together in a similar manner. The fasteners can be removed at any time so that the eye may be opened and the condition of the eye assessed by the ophthalmic practitioner. The eye may be resealed by reattaching the fasteners to the ends of the connecting means in the manner previously described.

It is also an object of the present invention to provide a method for using a tarsorrhaphy device. Initially, an injection of a local anesthetic such as 1–2% lidocaine is injected into the upper eyelid using a hypodermic needle. The site of the injection should be located approximately where the center of a tarsorrhaphy clip will be after it has been attached to the eyelid. A raised blister on the upper eyelid results from the injection. The injection needle is then passed fully through the raised blister and made to exit through the skin at a point parallel to the eyelid margin approximately 5–10 mm from the entrance site, the distance being approximately equivalent to the length of the connecting means.

A hypodermic needle is used as the injecting needle which has an adequate internal diameter to accommodate the tube. The injecting needle is then used as a means to introduce the first tube under the skin along the eyelid margin. The first tube is inserted into one end of the injecting needle and fed into the needle until the first end of the tube which had been inserted into the needle projects from the tip of the needle. The protruding first end of the tube is held firmly and the needle removed from the blister, leaving the first tube inserted through the raised blister, with the first and second ends extending from each of the needles' exit and entrance sites, respectively. The first connecting means is then placed between the ends of the first tube and a portion of the tube proximate to its first end is attached to the first end of the first connecting means, preferably by means of a jawed clamp attached to the first end of the connecting means. If the jaws of the clamp are not self-locking, a cap may be placed over the ends of the jaws to hold the jaws firmly together. The tube is then drawn taut, and a portion of the tube proximate to the second end of the tube is then clamped firmly between the opposing locking jaws of the jawed clamp attached to the second end of the connecting means. A second cap may be placed over the ends of the jaws, if required. At this point, the first connecting means is secured in position along the margin of the upper eyelid. The first connecting means is approximately parallel to a palpebral fissure.

The identical procedure is then conducted on the lower eyelid, concluding with portions of the second tube of the lower eyelid being held securely in the jawed clamps attached to each end of the second connecting means. The eye is then closed, and the connecting means are then situated directly adjacent and approximately parallel to one another across the palpebral fissure. The first ends of the first and second connecting means are fastened together in a reversible manner, preferably with one or more elastic bands. Similarly, the second ends of the first and second connecting means are then fastened together in a reversible manner.

It is another object of the present invention to provide a method for performing a temporary tarsorrhaphy comprising inserting a first tube having first and second ends through a portion of the upper eyelid of an eye in a linear fashion so that a portion of the tube lies beneath the skin of the eyelid and the first and second ends of the tube protrudes from the eyelid. A second tube having first and second ends is inserted through a portion of the lower eyelid of the eye in a similar fashion so that the first and second ends of the second tube also protrude from the lower eyelid. The first ends of the first and second tubes are directly fastened together in a reversible manner. The second ends of the first and second tubes are then directly fastened together in a reversible manner to narrow the palpebral fissure and complete the temporary tarsorrhaphy.

Another object of the present invention is to provide a device for forming a temporary tarsorrhaphy comprising a first tube at least partially embedded in an upper eyelid, having a first end and a second end which protrude from the upper eyelid, and a second tube at least partially embedded in a lower eyelid having a first end and a second end which protrude from the lower eyelid. The first ends of the first and second tubes are drawn and fastened directly together via tying, heat fusing, or other reversible methods known in the art. The second ends of the first and second tubes are then drawn and fastened directly together in a reversible manner by the means previously described.

An additional object of the present invention is a method for performing a temporary tarsorrhaphy comprising implanting a first tube having first and second ends in an upper eyelid of an eye so that a portion of the tube lies beneath the skin of the eyelid, and having the first and second ends of the tube protruding from the upper eyelid. A second tube is then implanted in the lower eyelid of an eye so that a portion of the second tube is subcutaneous and the first and second ends of the second tube protrude from the lower eyelid. The first ends of the first and second tubes are drawn and secured together in a reversible manner with a fastener. The second ends of the first and second tubes are then drawn and secured together in a reversible manner with a second fastener to complete the temporary tarsorrhaphy.

A further object of the present invention is a device for performing a temporary tarsorrhaphy comprising a first tube having first and second ends which may be inserted through a portion of the upper eyelid of an eye so that a portion of the tube lies beneath the skin of the eyelid, having the first and second ends of the tube protruding from the upper eyelid. The device also comprises a second tube having first and second ends which may be inserted through a portion of the lower eyelid of the eye such that the first and second ends of the second tube also protrudes from the lower eyelid. Optionally, each tube may be hollow and include a means for stiffening each tube such as a wire, needle, or similar material which may be inserted through the tube to add rigidity and/or strength to the tube. A first clamping means for drawing and securing together in a reversible manner the first ends of the first and second tube is attached proximate to the first ends of the first and second tubes. A second clamping means for drawing and securing together in a reversible manner the second ends of the first and second tubes is then attached to the second ends of the tubes. The clamping means are preferably jawed clamps.

An additional object of the present invention is a method for performing a temporary tarsorrhaphy comprising implanting a first tube having first and second ends in an upper eyelid so that a portion of the tube lies beneath the skin of the eyelid and the first and second ends of the first tube protrude from the upper eyelid. A second tube having first and second ends is then inserted through a portion of the lower eyelid of an eye so that a portion of the tube lies beneath the skin of the eyelid and the first and second ends protrude from the upper eyelid. The first ends of the first and second tubes are fastened directly together in a reversible fashion. The second ends of the first and second tubes are then drawn and secured together in a reversible manner with a clamping means to complete the temporary tarsorrhaphy.

Still another object of the present invention is a device for performing a temporary tarsorrhaphy comprising a first tube having first and second ends which may be inserted in a linear fashion through a portion of the upper eyelid of an eye so that a portion of the tube lies beneath the skin of the eyelid and the first and second ends protrude from the upper eyelid. The device further comprises a second tube which may be inserted through a portion of the lower eyelid of the eye such that the first and second ends of the second tube also protrude from the lower eyelid. The first ends of the first and second tubes are fastened directly together in a reversible fashion. A clamping means for drawing and securing together the second ends of the first and second tubes in a reversible manner is then attached to the second ends of the tubes.

Yet another object of the present invention is a device that reduces the complications associated with performing a temporary tarsorrhaphy. In the furtherance of this and other objectives, a temporary tarsorrhaphy assembly is provided which comprises a shaft that is suitable for mounting on either the upper or lower eyelid of an eye. Unlike the clip of the other embodiments, which comprise a tube and a connecting means, the shaft of this embodiment consists of a solid, non-cylindrical, non-venued (i.e., interior solid and not substantially hollow) elongated member having a center bar and two terminal ends, each end preferably defining a small latitudinally oriented aperture therethrough. In performing a temporary tarsorrhaphy, one shaft for each eyelid is utilized. Each shaft is mounted on its respective eyelid by a tube as previously described. In a preferred embodiment, the tube loops over a portion of a first terminal end of a first shaft and is threaded through apertures on that shaft such that the tube secures the terminal end of that shaft to the upper eyelid. Alternatively, each end of the tube is secured to an end of the shaft by tying an end of the tube around a terminal end of the shaft. This procedure is repeated on the opposite ends of the first and second shafts using two separate tubes.

At least one fastener is provide which is disposed around each shaft for reversibly drawing and securing together portions of the first and second shaft. In a preferred embodiment, a first and second fastener are disposed around opposing terminal ends of the first and second shafts for reversibly drawing and securing together portions of the first and second shafts. Alternatively, first and second fasteners may be disposed around opposing terminal ends of the first and second shaft for reversibly drawing and securing together portions of the first and second shaft. In a preferred embodiment, terminal ends of each shaft have a dumbbell shape whereby the dumbbell shaped terminal end portions of each shaft prevent the fastener from disassociating from the terminal ends when the assembly is in the mounted position. In the assembly in accordance with the present invention, the fastener is comprised of a material selected from the group consisting of plastic, rubber, silicone, suture thread and metal, most preferably the fastener is an elastic band. For ease of use and comfort for the user, each shaft may be adapted to comprise a padded center bar.

Further objects, features and advantages of the invention will be apparent from the following detailed non-limiting description when taken in conjunction with the accompanying drawings.

DETAILED DESCRIPTION OF THE INVENTION

In accordance with the present invention, one embodiment of a tarsorrhaphy device is a pair of clips each comprising a tube which is surgically implanted in a linear fashion in an eyelid such that the tube has a subcutaneous center portion and end portions which protrude from the eyelid. Portions of the protruding ends of each tube are fastened together with a connecting means having first and second ends, or alternatively, by means of a shaft. The temporary tarsorrhaphies are performed by mounting a tarsorrhaphy clip on each of the upper and lower eyelids of an eye and securing the first ends of the first and second connecting means together by means of one or more fasteners. The second ends of the first and second connecting means are secured together in a similar fashion to complete the temporary tarsorrhaphy. The connecting means or shaft are secured together in a reversible manner using such fasteners as elastic bands, wires, or other connecting materials which may be easily removed and replaced in order to allow the eye to be opened at will and inspected by the ophthalmic practitioner.

A tarsorrhaphy clip comprises a tube and a connecting means or shaft. Any tube utilized for performing a temporary tarsorrhaphy according to the present invention consists of a section of metal, plastic, rubber, silicone, wire, suture thread or similar material, any of which may optionally be sheathed by a nonabrasive coating, or other similar biocompatible materials known in the art that are durable and exhibit a high tensile strength while maintaining a very narrow diameter. The diameter of the tubing should be less than 300 microns, preferably 100–200 microns, and have a length of approximately 10–20 mm. The preferred material is silicone It must be noted, however, that a tarsorrhaphy shaft completed in accordance with the present invention may comprise a solid, preferably non-cylindrical, non-venued (i.e., interior solid and not substantially hollow) elongated member having a center bar and two terminal ends. Each of the terminal ends preferably defines a small latitudinally oriented aperture therethrough. In performing a temporary tarsorrhaphy, one shaft for each eyelid is utilized. In a preferred embodiment, each shaft is about 22 mm in length and about 4 mm in height and 2 mm in width.

Figure 1:
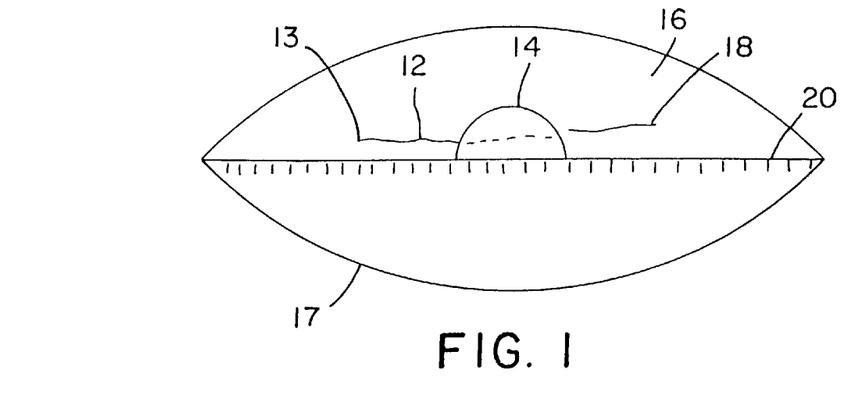
FIG. 1 is a front view of a closed eye having a first tube inserted through a raised blister on the upper eyelid.

A first tarsorrhaphy clip is mounted on the upper eyelid of an eye as follows. The first end 13 of a first tube 12 is passed through a raised portion 14 of the upper eyelid 16 of eye 17 such that approximately 5 to 10 mm of the tube 12 is beneath the surface of the upper eyelid, as shown in FIG. 1. The first tube 12 is now positioned so that the central 5 to 10 mm of the tube 12 lies beneath the surface of the upper eyelid 16 and the first end 13 and second end 18 of the tube 12 are roughly parallel to the eyelid margin 20.

Figure 2:
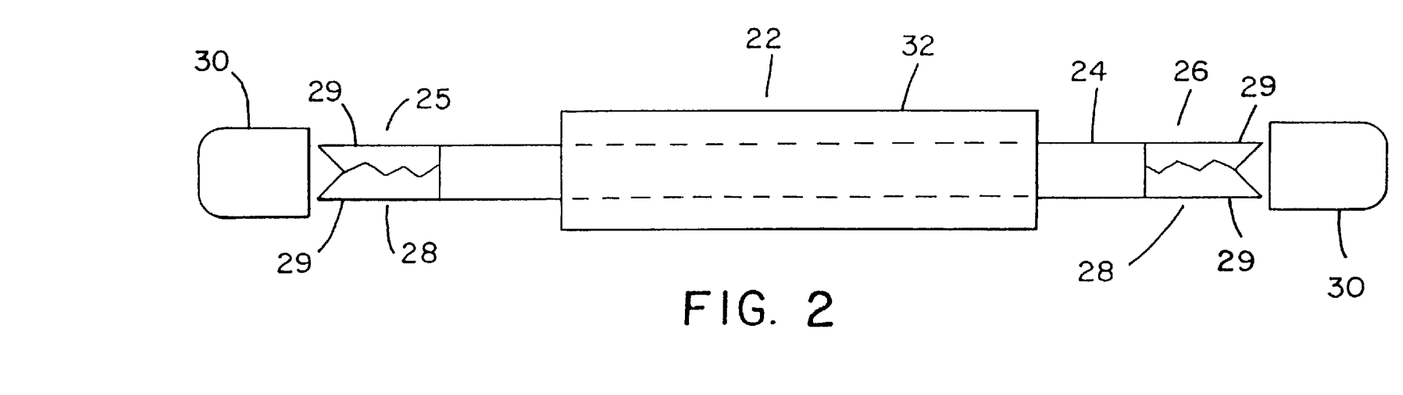
FIG. 2 is a top view of a connecting means in accordance with the present invention.

A first connecting means 22 as illustrated in FIG. 2 is then used to secure portions of the tube 12 proximate to the first and second ends. A connecting means comprises a rod to which the ends of the tubes may be secured. In preferred embodiments, each end of the connecting means will have a holding means attached thereto consisting of jawed clamps, wires, spring clips or other similar holding means known in the art. The connecting means 22 comprises a rod 24 having a first end 25 and a second end 26. The rod 24 consists of plastic, stainless steel, or other biocompatible material. The preferred material is stainless steel. The rod 24 has a preferred thickness of 25 to 22 gauge, and is approximately 5–10 mm in length. At each end of the rod 24 is a holding element 28. As illustrated, each holding element 28 consists of an opposable set of jawed members 29 which may be brought together in an interlocking fashion to secure a portion of a tube. Alternative holding elements may consist of pressure clamps, or any other means known in the art for firmly securing wires, tubes or similar materials. The jawed members 29 may be self-locking, or may be held closed by any method commonly known in the art, for example, caps, wires or spring clips. The preferred material for closing the jawed members which are not self-locking is a cap. As shown in FIG. 2, the jawed members 29 are secured with caps 30. Caps 30 comprise rubber, plastic or other suitable materials which may be slid or screwed over the closed jawed members 29 in order to securely close and lock the members 29, as well as protect the eyelid from being injured by the tips of the jawed members 29.

The connecting means 22 may optionally be partially ensconced in a cylindrical sleeve 32 which covers the central portion of the connecting means 22, as illustrated in FIG. 2. The sleeve 32 comprises a soft cushion of foam, rubber, plastic or other similar material which helps protect the eyelid from abrasion by the connecting means 22. The preferred materials are foam and rubber. The caliber of the connecting means with cushion sheath 32 is preferably 20 or 18 gauge.

Figure 3:
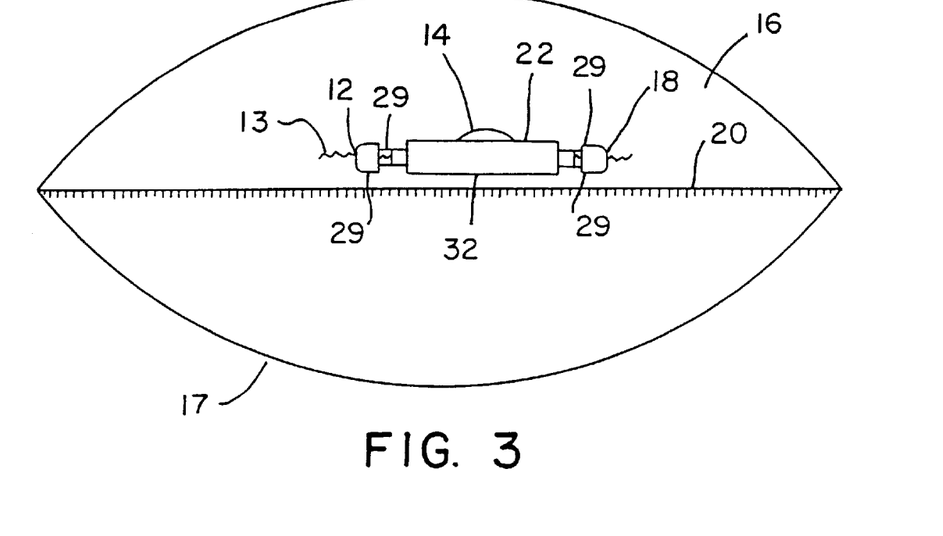
FIG. 3 is a front view of an eye illustrating a mounted tarsorrhaphy clip in accordance with the present invention.

As shown in FIG. 3, a portion of tube 12 proximate to first end 13 is attached to the connecting means 22 by enclosing it between the jawed members 29 attached to the first end 25 of connecting means 22. The term "proximate" is herein defined as any portion of the tube which lies between the point at which the tube exits the eyelid and the end of the tube. The jawed members 29 are closed to firmly grasp a portion of tube 12. Cap 30 is then placed over the ends of the jawed members 29 to prevent the members from opening. Tube 12 is pulled taut, and jawed members 29 attached to second end 26 of the connecting means 22 are clamped to a portion of the tube 12 proximate the second end 18 of the tube 12. Cap 30 is placed over jawed members 29 attached to second end 26 in the manner previously described to secure the first connecting means 22 to the upper eyelid 16.

Figure 4:
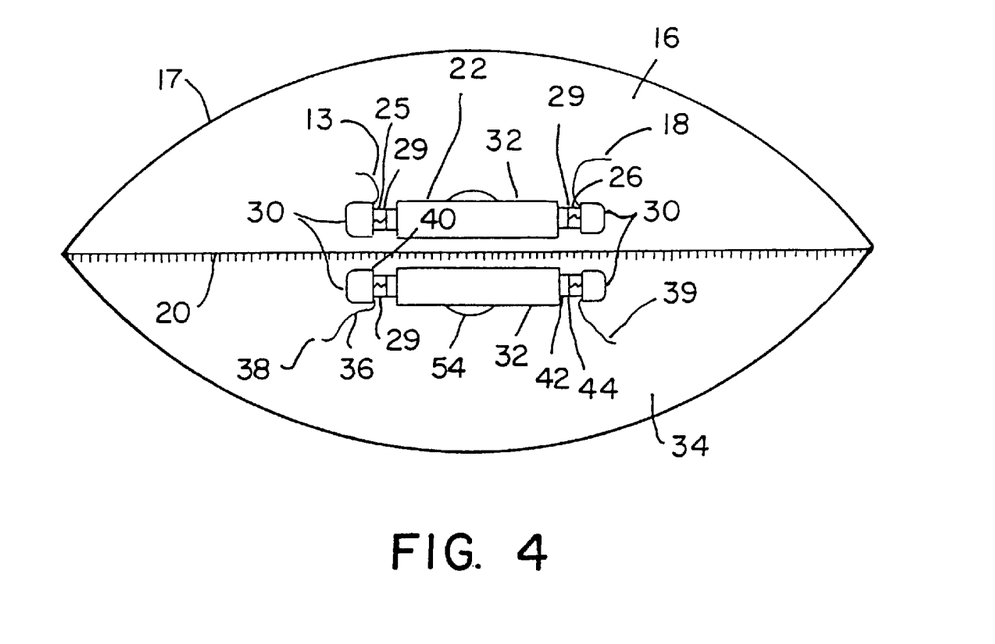
FIG. 4 is a front view of an eyelid having two tarsorrhaphy clips mounted parallel to each other.

As shown in FIG. 4, the procedure is repeated using lower eyelid 34, with a second tube 36 having a first end 38 and a second end 39 being partially implanted under the lower eyelid 34 such that a portion of the tube 36, preferably 5–10 mm, is subcutaneous. After implantation, tube 36 lies approximately parallel to the eyelid margin 20. A portion of the second tube 36 proximate the first end 38 is firmly clasped between the jawed members 29 attached to a first end 40 of a second connecting means 42. The jawed members 29 are locked closed with the cap 30. Second tube 36 is drawn taut. A portion of tube 36 proximate the second end 39 is firmly secured between the jawed members 29 at the second end 44 of the second connecting means 42, and the cap 30 placed over the jaws 29 as previously described.

Figure 5:
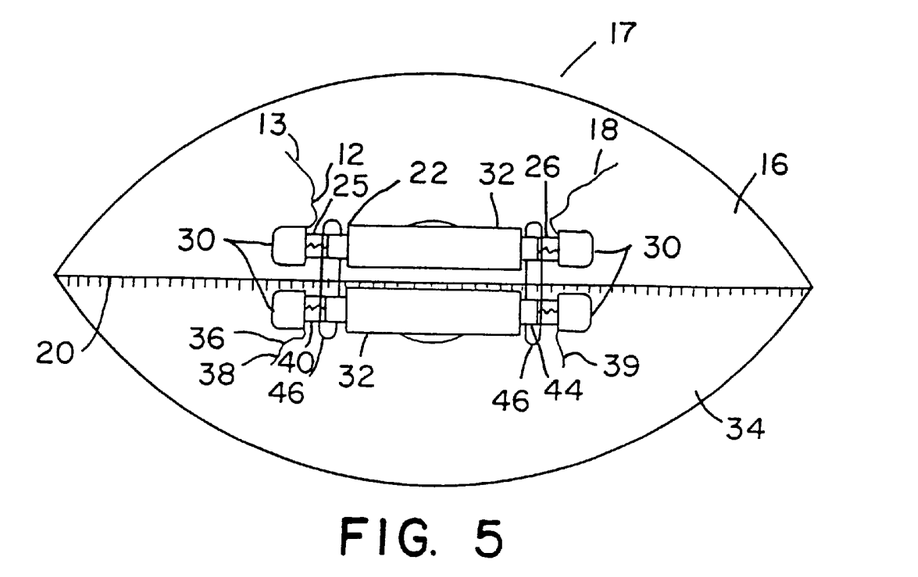
FIG. 5 is a front view illustrating a temporary tarsorrhaphy completed in accordance with the present invention.

The eye is then closed, allowing the connecting means 22 and 42 to lie roughly parallel to each other across the palpebral fissure. The first ends 25 and 40 of the connecting means 22 and 42, respectively, are secured together in a reversible fashion using one or more fasteners 46, as shown in FIG. 5. Such fasteners may consist of clamps, elastic bands, wires, or other suitable materials known in the art. The preferred fastener is a small elastic band such as rubber bands used in orthodontia. One or more fasteners 46 are then used to secure the second ends 26 and 44 of the connecting means 22 and 42, respectively, together in a reversible fashion. Alternatively, the connecting means 22 and 42 may be held together by placing one or more fasteners around the center portion or other parts of both connecting means. The fasteners 46 may be removed periodically so that the eye 17 may be opened and inspected. After inspection of the eye 17, the fasteners 46 are then reattached.

The method of the present invention comprises the insertion of a first tube through a portion of the upper eyelid of an eye so that a portion of the tube lies beneath the skin of the upper eyelid and each end of the first tube protrudes from the upper eyelid. A second tube having first and second ends is then inserted through a portion of the lower eyelid of the eye so that a portion of the second tube is subcutaneous while allowing each end of the second tube to protrude from the lower eyelid. The first ends of the first and second tubes are drawn and secured together in a reversible manner. The second ends of the first and second tubes are then drawn and secured in a reversible manner. Drawing and securing the tubes together may be accomplished by directly fastening the first ends and the second ends of the tubes together respectively, or by use of connecting means or clamping means described herein or any feasible combination thereof.

Figure 6:
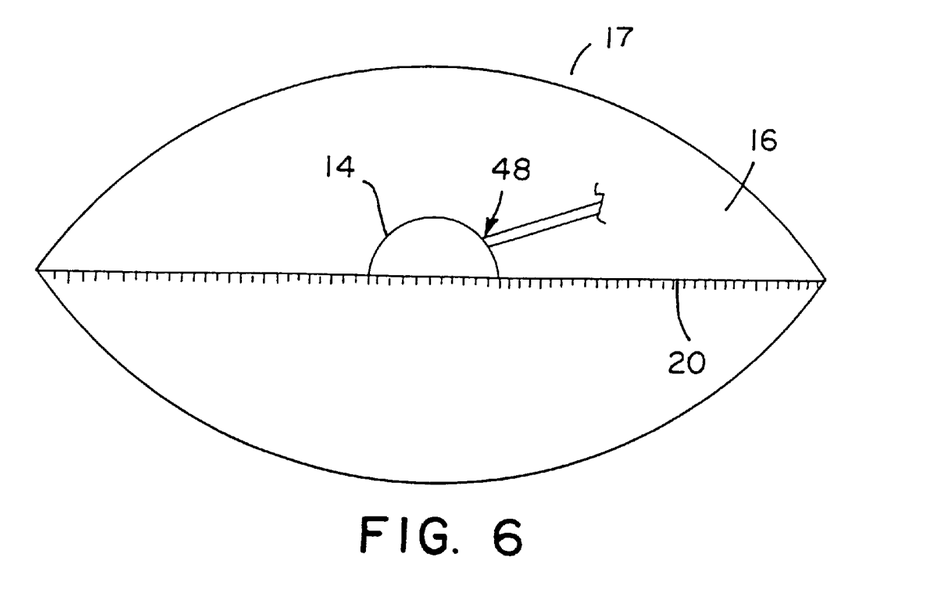
FIG. 6 is a front view of a raised blister being formed on an upper eyelid by subcutaneous injection of an anesthetic.

An illustration of a method of the present invention is as follows. As shown in FIG. 6, the tip of a hypodermic needle 48 is inserted beneath the skin of the upper eyelid 16. An anesthetic, preferably 1 or 2% lidocaine, is injected beneath the eyelid skin near eyelid margin 20, to raise a blister 14 beneath the skin. The hypodermic needle 48 has an appropriate internal diameter so as to adequately accommodate the diameter of the tubes 12 and 36.

Figure 7:
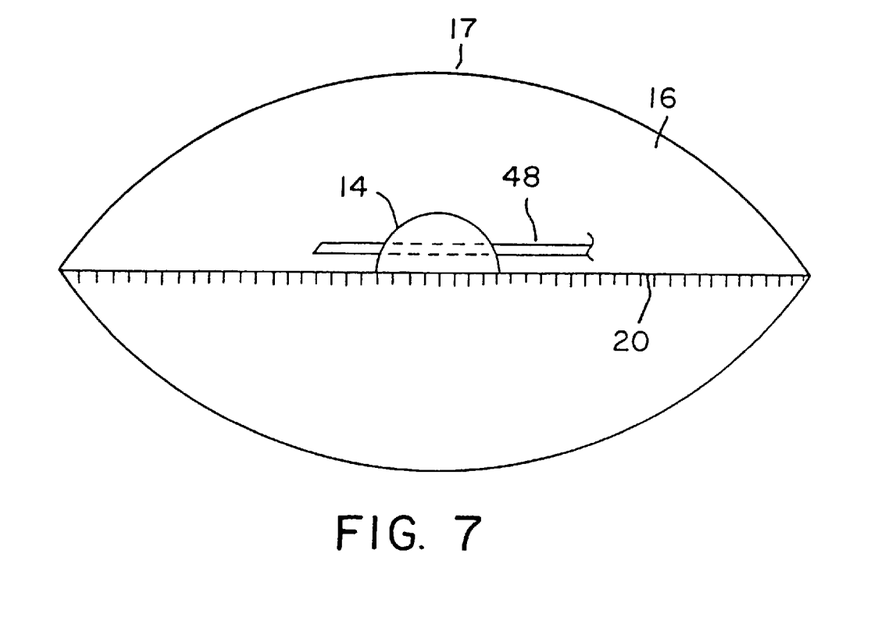
FIG. 7 is a front view of an injecting needle passed through a raised blister on an upper eyelid parallel to the eyelid margin.

The hypodermic needle 48 is then passed into the blister 14 which has been created by the local anesthetic and directed parallel to the eyelid margin 20. The needle 48 is then made to exit through the blistered skin at a point along the eyelid margin approximately 5–10 mm from the entrance site as shown in FIG. 7. This distance will be approximately the same as the length of the connecting means 22 and 42.

Figure 8:
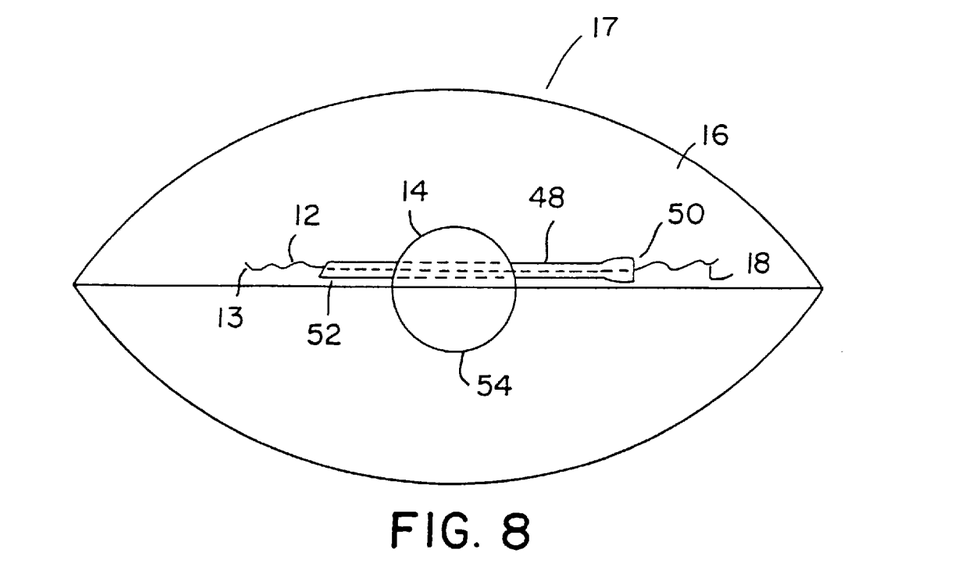
FIG. 8 is a front view of a tube being passed through a hypodermic needle that has been inserted through a raised blister on the upper eyelid.

The hypodermic needle 48 is then used to introduce the first tube 12 into place. The tube 12 is inserted into the first end 50 of hypodermic needle 48, and threaded through hypodermic needle 48 until it emerges from tip 52 as shown in FIG. 8. The hypodermic needle 48 is then carefully removed, leaving tube 12 in place, such that approximately 5–10 mm of the tube 12 is subcutaneous. As shown in FIG. 8, the ends 13 and 18 of the tube 12 protrude from each side of the raised blister 14.

The first connecting means 22 is then placed between the ends of the first tube 12. The jawed members 29 located at first end 25 of connecting means 22 are then closed around a portion of the first tube 12 proximate to the first end 13. The cap 30 is placed over the jawed members 29 to firmly close and lock the jawed members 29 at first end 25 to firmly hold a portion of the tube 12. The tube 12 is pulled taut, and the jawed members 29 attached to the second end 26 of the connecting means 22 are closed around a portion of the tube 12 proximate to the second end 18. The cap 30 is placed over the end of the jawed members 29 to securely close and lock the jawed members 29. The steps are then repeated with the lower eyelid 34. Hypodermic needle 48 is used to create a second blister 54 on the lower eyelid 34, and the second tube 36 is threaded through the second blister 54 in the manner previously described, as shown in FIG. 8. A portion of the second tube 36 proximate the first end 38 is firmly clasped between the jawed members 29 attached to first end 40 of the second connecting means 42. The jawed members 29 are locked closed with the cap 30, as shown in FIG. 4. The second tube 36 is drawn taut, and a portion of the tube 36 proximate the second end 39 is firmly secured between the jawed members 29 located at the second end 44 of the second connecting means 42. The cap 30 is placed over the jawed members 29 as previously described.

The connecting means 22 and 42 are then in position along the margin 20 of each of the upper and lower eyelids when the eye 17 is closed, as shown in FIG. 4. The connecting means are directly adjacent and roughly parallel to one another across the eyelid margin 20. Finally, one or more fasteners 46 preferably consisting of one or more elastic bands are used to secure the first ends 25 and 40 of the connecting means 22 and 42, respectively, together in a reversible fashion as shown in FIG. 5. Identical fasteners 46 are used to secure second ends 26 and 44 together in a reversible manner. The fasteners 46 may be easily removed when required so that the eye may be inspected. Alternatively, one or more fasteners 46 may be placed about the center portion of the first and second connecting means 22 and 42, respectively, to secure the connecting means together. This allows easy, safe and convenient periodical inspection of the eye to be accomplished, without requiring additional surgery each time the temporary tarsorrhaphy needs to be undone.

Alternatively, a method of the present invention comprises the steps of mounting to a portion of an upper eyelid 16 a first shaft 100 and to a portion of a lower eyelid a second shaft 100 and fastening the first and second shafts 100 together in a reversible manner as illustrated in FIGS. 12–15. In such alternative method, as shown in FIGS. 12–15, the above illustration pertains except that the tubes 12 and 36 are sutured to the shafts 100 rather than held in place though such clamps. Preferably, shafts 100 define at least one aperture at a terminal end to assist with suturing.

Figure 9:
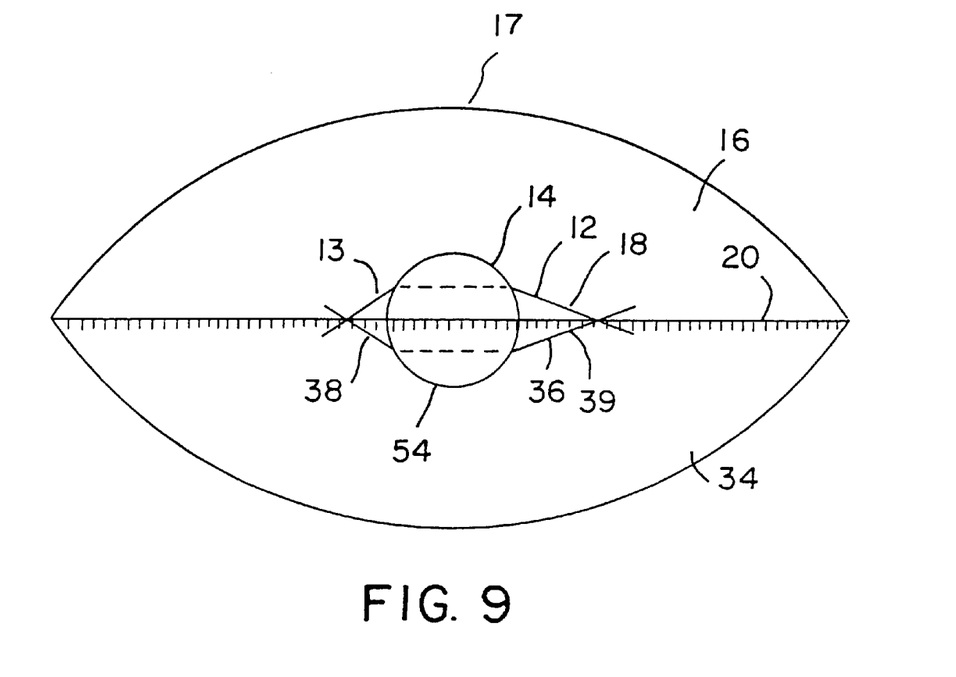
FIG. 9 is a front view illustrating an alternative embodiment of a temporary tarsorrhaphy completed in accordance with the present invention.

In another alternative embodiment of the present invention, tube 12 and tube 36, respectively, are implanted in the upper 16 and lower 34 eyelids of an eye in the manner previously described. The first ends 13 and 38 of the tubes 12 and 36, respectively, are directly fastened together in a reversible manner as shown in FIG. 9. The fastening may consist of tying the tubes together directly or interlinking the tube ends or heat sealing the tube ends together, or any other similar means for fastening which allow the first ends and second ends of the tubes to be attached in a reversible manner so that the physician may inspect the eye as required. In a similar fashion, the second ends 18 and 39 of the first and second tubes 12 and 36, respectively, are fastened together in a similar manner to complete the temporary tarsorrhaphy. Note that although the first ends of the tubes are both illustrated as lying adjacent to each other, the first ends of the tubes may lie opposite one another, in this and the following alternative embodiments.

Figure 10:
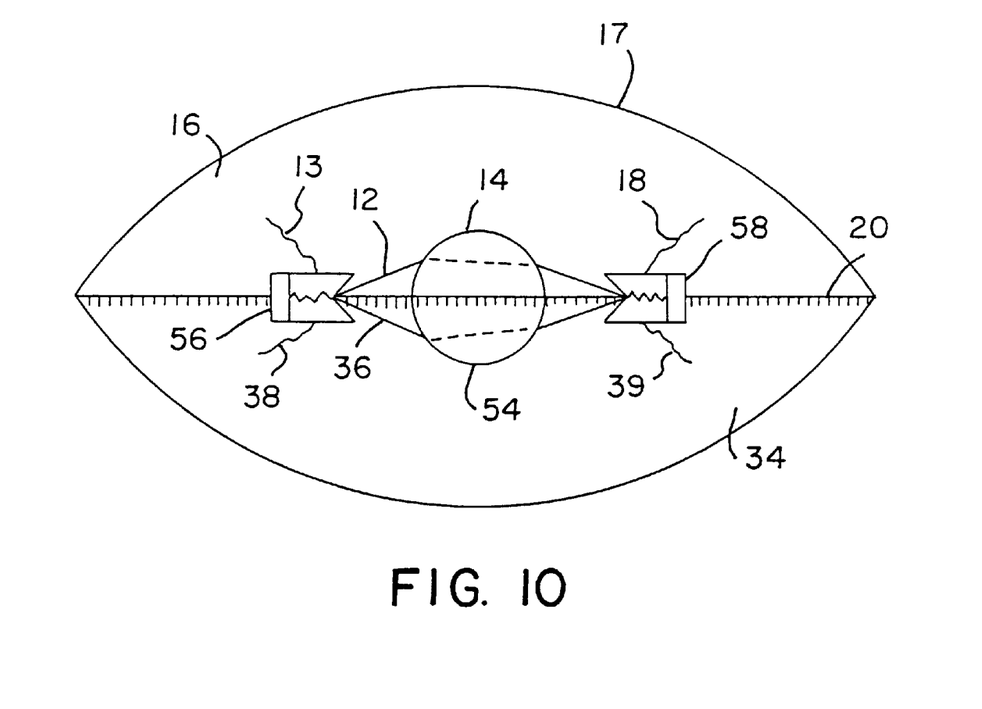
FIG. 10 is a front view illustrating a second alternative embodiment of a temporary tarsorrhaphy completed in accordance with the present invention.
Figure 11:
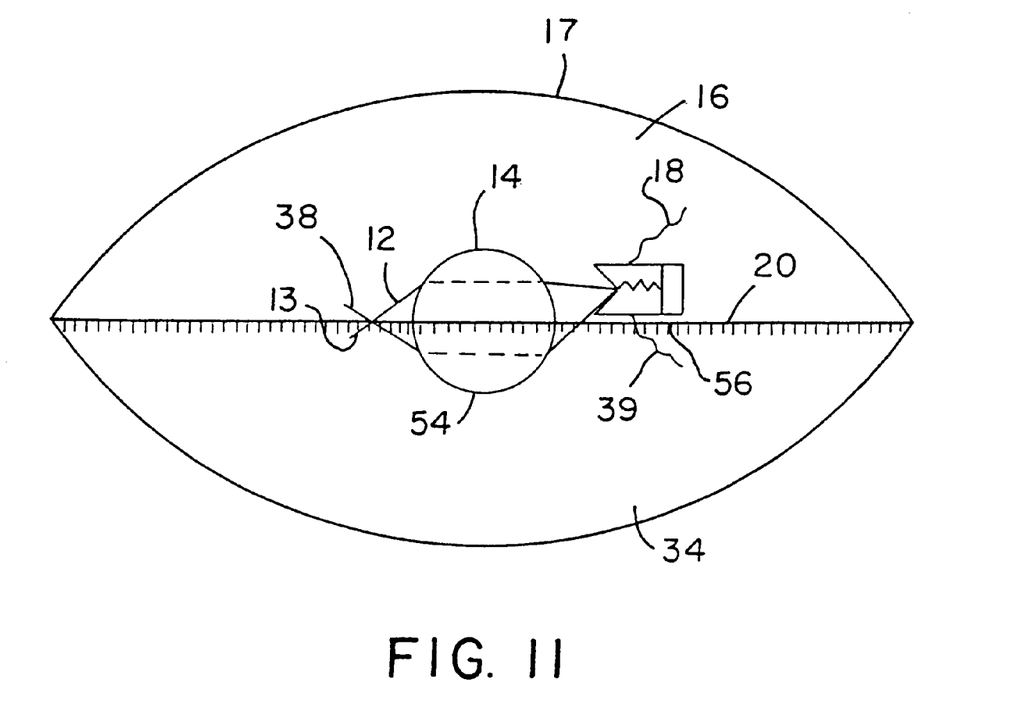
FIG. 11 is a front view illustrating a third alternative embodiment of a temporary tarsorrhaphy completed in accordance with the present invention.

In another alternative embodiment, as shown in FIG. 10, the first ends 13 and 38 of the first and second tubes 12 and 36, respectively, may be drawn and held together by first clamping means 56. Second ends 18 and 39 of the first and second tubes may be drawn and held together by a second clamping means 58. Clamping means 56 and 58 may comprise jawed clamps, as illustrated, or may comprise spring clamps, wire, or other means known or used in the art which may be used to firmly draw and hold together the first ends of the first and second tubes. Alternatively, clamping means 56 and 58 may be similar to the connecting means 22 and 42 previously described, comprising a rod with first and second ends and a holding element at each end.

In another alternative embodiment, the tubes 12 and 36 are implanted in the eye 17 in the manner previously described. The first ends 13 and 38 of the first and second tubes 12 and 36, respectively, may be directly fastened together in a reversible manner by tying, interlinking or heat fusing the tube ends together, or other similar methods. The second ends 18 and 39 of the first and second tubes may be drawn and held together by a clamping means or connecting means, as previously described.

Figure 13:
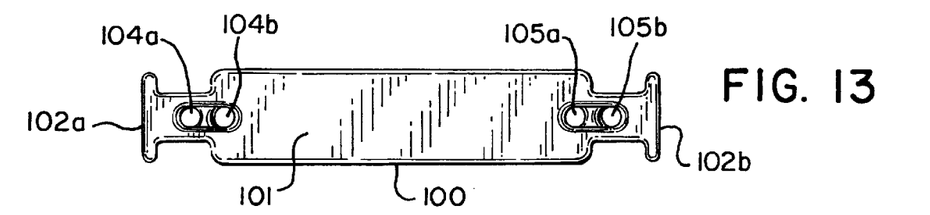
FIG. 13 is a top view illustrating the dimensions of an alternative embodiment of a shaft in accordance with the present invention.
Figure 14:
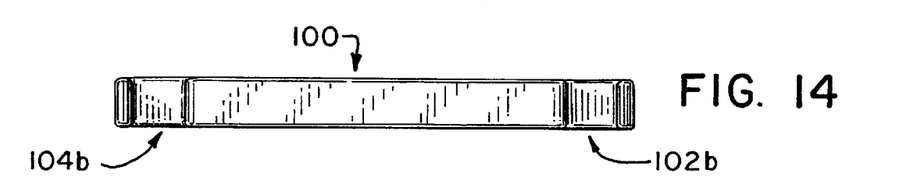
FIG. 14 is a side view illustrating the dimensions of an alternative embodiment of a shaft in accordance with the present invention.
Figure 15:
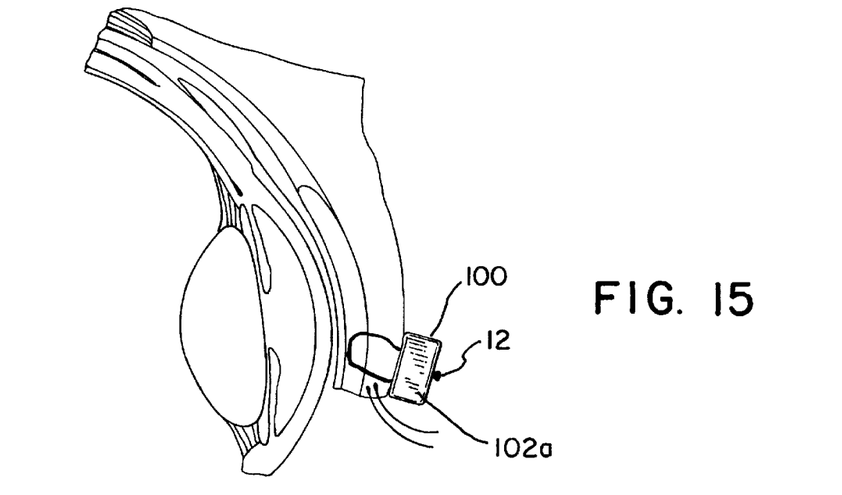
FIG. 15 is a cross-sectional view illustrating an embodiment of a shaft in accordance with the present invention, in use.

Yet another alternative embodiment provides a shaft 100 that is suitable for mounting on either the upper or lower eyelid of an eye, as seen in FIGS. 12–15. In the alternative embodiment, the assembly for performing the temporary tarsorrhaphy will comprise a first shaft and a second shaft together with either one or more tubes for securing the shafts to eyelids or the assembly may additionally comprise one or more fasteners for reversibly drawing and screwing together portions of the shafts once the shafts are secured into position on the patient's eyelids. Alternatively, an assembly for performing a temporary tarsorrhaphy may include both one or more tubes together with one or more fasteners in combination with a first and second shaft. Additionally, the connecting means may be substituted for a shaft in an assembly according to the present invention. Unlike the clip of the other embodiments which comprises a connecting means, the shaft 100 of this embodiment consists of a solid, preferably non-cylindrical, non-venued (i.e., interior solid and not substantially hollow) elongated member having a center bar 101 and two terminal ends 102a and 102b. Each end may be solid, or as shown in the preferred embodiments of FIGS. 12–15, define at least one small latitudinally oriented aperture therethrough. In performing a temporary tarsorrhaphy, one shaft 100 for each eyelid is utilized. Each shaft 100 is mounted on its respective eyelid by tubes 12 and 36, or by any other convenient means known in the art. In a preferred embodiment, tube 12 loops over a portion of terminal end 102a and is threaded through apertures 104a and 104b such that the tube 12 secures terminal end 102a of clip 100 to the eyelid as shown in FIG. 15. Additionally, the tube 12 loops over a portion of terminal end 102b and is threaded through apertures 105a and 105b such that the tube 12 secures terminal end 102b of shaft 100 to the eyelid.

Figure 12:
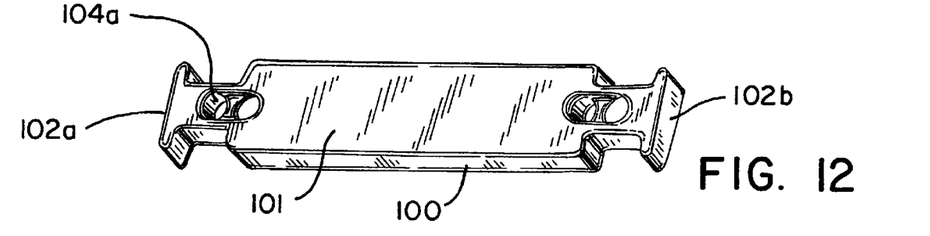
FIG. 12 is a top perspective view illustrating an alternative embodiment of a shaft in accordance with the present invention.

At least one fastener 46 is provided which is disposed around each shaft 100 for reversibly drawing and securing together portions of each shaft 100. In a preferred embodiment, a first fastener 46 is disposed around opposing terminal ends 102a of the first and second shafts 100 for reversibly drawing and securing together portions of the first and second shafts 100 and a second fastener 46 is disposed around opposing terminal ends 102b of first and second shafts 100 for reversibly drawing and securing together portions of the first and second shafts. In a preferred embodiment, terminal ends 102a and 102b have a dumbbell shape whereby the dumbbell shaped terminal end portions 102a and 102b of each shaft 100 prevent the fastener 46 from disassociating from the terminal ends 102a and 102b when the assembly is in the mounted position as shown in FIGS. 12–14. In the assembly in accordance with the present invention, the fastener 46 is comprised of a material selected from the group consisting of plastic, rubber, silicone, suture thread and metal, most preferably the fastener 46 is an elastic band. In the preferred embodiment, the fastener 46 is a material which may be reversibly fastened numerous times, including, but not limited to, an elastic or rubber band. For ease of use and comfort for the user, each shaft 100 may be adapted to comprise a padded center bar 101. In a preferred embodiment, shaft 100 is preferably about 22 mm in length and about 4 mm in height and about 2 mm in width.

It is understood that the invention is not confined to the particular embodiments set forth herein as illustrative, but embraces all such forms thereof as come within the scope of the following claims.

What is claimed is:

1. An assembly for performing a temporary tarsorrhaphy comprising:
   (a) a first shaft comprising an elongated member having first and second terminal ends, the first shaft mountable on the upper eyelid of an eye;
   (b) a first tube for securing the first shaft to the upper eyelid of an eye;
   (c) a second shaft comprising an elongated member having first and second terminal ends, the second shaft mountable on the lower eyelid of an eye;
   (d) a second tube for securing the second shaft tot he lower eyelid of an eye; and
   (e) at least one fastener which may be disposed around the first and second shaft for reversibility drawing and securing together portions of the first and second shafts.

2. The assembly of claim 1 further comprising two fasteners.

3. The assembly of claim 1, wherein the terminal ends of the first and second shafts are dumbbell shaped.

4. The assembly of claim 2, wherein each of the first and second fasteners are elastic bands.

5. The assembly of claim 1, wherein each of the first and second tubes is comprised of a material selected from the group consisting of plastic, rubber, silicone, suture thread and metal.

6. The assembly of claim 1, wherein each of the first and second shafts is comprised of a material selected from the group consisting of plastic, rubber, silicone, and metal.

7. The assembly of claim 1, wherein at least one terminal end of a shaft further defines at least one aperture.

8. The assembly of claim 7, wherein first and second terminal ends of each shaft each define at least one aperture.

9. An assembly for performing a temporary tarsorrhaphy comprising:
   (a) a first shaft which may be mounted on an upper eyelid of an eye, the first shaft having a center bar and first and second dumbbell shaped terminal ends, each end defining at least one aperture disposed between each end and the center bar;
   (b) a second shaft which may be mounted on an lower eyelid of an eye, the second shaft having a center bar and first and second dumbbell shaped terminal ends, each end defining at least one aperture disposed between each terminal end and the center bar;
   (c) at least one fastener for drawing and securing together portions of the first and second shafts;
   whereby the dumbbell shaped terminal end portions of the first and second shafts prevent the fastener from disassociating from the terminal ends when the assembly is in the mounted position.

10. The assembly of claim 9, wherein the assembly comprises a first and second fastener, the first fastener for drawing and securing together portions of the first shaft and the second shaft proximate the first terminal end of each shaft; and the second fastener for drawing and securing together portions of the first shaft and the second shaft proximate the second terminal end of each shaft.

11. The assembly of claim 9, further comprising a tube for securing each shaft to an eyelid.

12. The assembly of claim 11, wherein each tube is a suture.

13. The assembly of claim 10, wherein each of the first and second fastener is comprised of a material selected from the group consisting of plastic, rubber, silicone, suture thread and metal.

14. The assembly of claim 13, wherein each of the first and second fastener is an elastic rubber band.

15. A shaft for performing a temporary tarsorrhaphy comprising:
   (a) a center bar; and
   (b) first and second terminal ends, each terminal end integrally attached to center bar defining at least one aperture disposed between each end and the center bar, such that the shaft has suitable dimensions for use in a temporary tarsorrhaphy.

16. The shaft of claim 15, wherein each terminal end has a dumbbell shape.

17. A shaft for performing a temporary tarsorrhaphy comprising:
   (a) a center bar; and
   (b) first and second terminal ends, each terminal end integrally attached to the center bar, and wherein each terminal end has a dumbbell shape, such that the shaft has suitable dimensions for use in a temporary tarsorrhaphy.

18. The shaft of claim 17, wherein at least one terminal end defines at least one aperture.

19. The shaft of claim 18, wherein each terminal end defines at least one aperture.

20. A method for performing a temporary tarsorrhaphy comprising:
   (a) inserting a first elongated hollow tube, having a first and a second end, through a portion of an upper eyelid in a linear fashion so that a portion of the tube lies beneath the skin of the eyelid and the first and the second ends of the tube protrude from the eyelid;
   (b) inserting a second elongated hollow tube, having a first and a second end, through a portion of a lower eyelid in a linear fashion so that a portion of the tube lies beneath the skin of the eyelid and the first and the second ends of the tube protrude from the eyelid;
   (c) fastening the first and second elongated hollow tubes together in a reversible manner.

21. The method of claim 20, step (c) further comprising the steps of:
   (i) drawing and directly fastening together the first ends of the first and second shafts in a reversible manner; and
   (ii) drawing and directly fastening together the second ends of the first and second shafts in a reversible manner to narrow the palpebral fissure in order to complete the temporary tarsorrhaphy.

22. The method of claim 20, steps (a) and (b) further comprising the steps of:
   (i) injecting a local anesthetic subcutaneously into the upper eyelid to produce a first raised blister of skin;
   (ii) passing a hypodermic needle completely through the first blister such that there is both an entrance and exit site of the needle in the first blister;
   (iii) feeding a first tube completely through the needle such that an end of the tube protrudes from each end of the needle;
   (iv) removing the needle from the first blister, leaving the first tube in place such that a portion of the first tube remains beneath the skin of the upper eyelid and each end of the tube protruding from the upper eyelid;
   (v) securing the first shaft on the upper eyelid by engaging each end of the protruding portions of the first tube with an end of the first shaft;
   (vi) injecting the local anesthetic subcutaneously into the lower eyelid to produce a second raised blister of skin;
   (vii) passing the hypodermic needle completely through the second blister such that there is both an entrance and exit site of the needle in the second blister;
   (viii) feeding the second tube completely through the needle such that an end of the securing means protrudes from each end of the needle;
   (ix) removing the needle from the second blister, leaving the second tube in place such that a portion of the second tube remains beneath the skin of the lower eyelid and each end of the second tube protruding from the lower eyelid; and
   (x) securing the second shaft on the lower eyelid by engaging each end of the protruding portions of the second tube with an end of the second shaft.

23. A method for performing a temporary tarsorrhaphy, comprising:
   (a) mounting a first shaft on an upper eyelid of an eye, the first shaft having a center bar and first and second dumbbell shaped terminal ends each end defining at least one aperture disposed between each end and the center bar;
   (b) mounting a second shaft on an lower eyelid of an eye, the second shaft having a center bar and first and second dumbbell shaped terminal ends each end defining at least one aperture disposed between each terminal end and the center bar;
   (c) drawing the first and second shafts together, in a reversible manner, with a fastener to narrow the palpebral fissure and complete the temporary tarsorrhaphy.

24. The method of claim 23, wherein step (c) further comprises the steps of:
   (i) drawing together portions of the first end of the first shaft proximate the first end of the second shaft with a first fastener; and
   (ii) drawing and securing together portions of the second end of the second shaft proximate the second end of the second shaft with a second fastener.

* * * * *